United States Patent [19]

Pannwitz

[11] 4,300,910
[45] Nov. 17, 1981

[54] TEST VIAL CONSTRUCTION AND METHOD OF MEASURING GAS, VAPOR AND AEROSOL COMPONENTS IN AN AIR SAMPLE

[75] Inventor: Karl-Heinz Pannwitz, Lübeck, Fed. Rep. of Germany

[73] Assignee: Drägerwerk Aktiengesellschaft, Fed. Rep. of Germany

[21] Appl. No.: 192,552

[22] Filed: Sep. 30, 1980

[30] Foreign Application Priority Data

Nov. 30, 1979 [DE] Fed. Rep. of Germany ....... 2948218

[51] Int. Cl.³ ...................... G01N 31/22; G01N 21/78
[52] U.S. Cl. .................................. 23/232 R; 422/59; 422/60; 422/61; 422/88
[58] Field of Search ................... 23/232 R; 422/58, 59, 422/60, 61, 88, 91

[56] References Cited

U.S. PATENT DOCUMENTS

| | | | |
|---|---|---|---|
| 2,908,555 | 10/1959 | Grosskopf | 23/232 R |
| 3,022,141 | 2/1962 | Grosskopf | 422/60 |
| 3,446,596 | 5/1969 | Salivar et al. | 422/58 X |
| 3,689,224 | 9/1972 | Agnew et al. | 422/61 |
| 3,740,196 | 6/1973 | Stroterhoff | 422/61 |
| 3,966,412 | 6/1976 | Stroterhoff | 23/232 R |
| 4,042,336 | 8/1977 | Larsson | 422/58 |

FOREIGN PATENT DOCUMENTS

1140749  12/1962  Fed. Rep. of Germany.

*Primary Examiner*—Ronald Serwin
*Attorney, Agent, or Firm*—McGlew and Tuttle

[57] ABSTRACT

A method of measuring gas, vapor and aerosol components in an air sample, using a gas detecting device, includes a glass tube having openable ends for the flow of test gas therethrough and a filter therein entraining components to be measured, comprises, breaking an ampoule of a liquid solvent for the materials entrained by the filter to cause the solvent to pass through the filter into a granular reaction layer and then through an empty chamber. The testing tube includes a liquid lock which is formed by a hydrophobic paper which is disposed downstream of the empty chamber so as to retain the reacting products in the chamber so they may be viewed. The reactant products undergo a color change in proportion to a substance to be detected, such as sulfuric acid, for example.

4 Claims, 1 Drawing Figure

U.S. Patent  Nov. 17, 1981  4,300,910
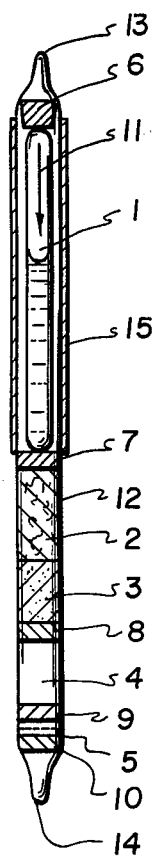

TEST VIAL CONSTRUCTION AND METHOD OF MEASURING GAS, VAPOR AND AEROSOL COMPONENTS IN AN AIR SAMPLE

FIELD AND BACKGROUND OF THE INVENTION

The present invention relates to devices for testing the presence of materials in air and other gases in general and, in particular, to a new and useful gas testing tube and method of measuring gas, vapor and aerosol components in an air sample.

A comprehensive assortment of test vials for quantitative rapid analysis of gases, vapors and aerosols in air in the range of the MAK number, the lower limit of inflammability and for technical gas analysis are available. For application, the tips of the test vials are broken off, the test vial is inserted into the gas detection pump and, with this, the prescribed gas volume is suctioned through the reaction layers. Most test vials are graduated tubes, where the indicator layer becomes discolored over a length, dependent upon the gas concentration. There are also test vials with a color comparator layer where, upon the reaction, a color comparison is made.

Test vials which contain one or even several breakable ampoules with liquid or gaseous reagents are also known. Here, the test vial is breakable in the area of the ampoule, which is covered over with a hose sleeve.

The ampoules provide the possibility of storing liquid or vaporized reagents in the test vial, without these materials coming into contact with the other granular fillings during the storage period. For purposes of application, the test vial is broken at the breakable area, always at the correct point in time for the reaction, whereby, the ampoule also breaks, and its contents empty into the interior of the test vial. The hose sleeve prevents the test vial from falling apart.

In one known procedure for the determination of chlorvinyl-arsenic (lewisite) by means of a test vial, the air to be examined is passed over a surface-active layer, such as silica-gel, which contains traces of water. The arsenic compounds formed from the chlorvinyl-arsenics are then brought into contact with nascent hydrogen, and the aresenic-hydrogen compounds thus formed are then detected by known procedures. For the production of nascent hydrogen, a metal powder or metal dust is placed in front of the surface-active layer and the ampoule containing sulphuric acid. Zinc dust, aluminum dust or similar substances can be used as the metal layer.

On breaking of the ampoule, sulphuric acid vapor penetrates the metal layer. The test vial is used as follows:

After breaking the tips, the air to be tested is suctioned into the test vial. If the air contains lewisite, this is broken down in the decomposition layer through the formation of arsenic and arsenic compounds. The ampoule is then broken and some more air is suctioned through the vial. This permits the sulphuric acid vapor to react with the metal. The hydrogen thus formed reacts with the arsenic in the presence of lewisite, which then leads to a discoloration in the known manner. The discoloration occurs on a solid carrier. The color substance formed occurs on this carrier in a large dilution, so that the color intensity in very small contaminant concentrations in the test air during a normal air sample flow can no longer be evaluated (See German Patent No. 1,140,749).

SUMMARY OF THE INVENTION

Since further constant reductions of the MAK values are to be expected, the present invention provides test vials with which even minute contaminant concentrations can be made clearly and safely recognizable.

The gas detection device, in accordance with the invention, comprises, an outer glass tube having a breakable tip at each end and having a closed breakable ampoule of a solvent material disposed upstream of an entraining filter, a reaction layer, an empty tube chamber and a liquid lock in that order.

In accordance with the method of the invention, the materials to be detected are entrained by the filter and the ampoule is broken to direct the solvent liquid therein through the filter to dissolve the materials therein and to pass them into a reaction layer to cause a color reaction. The color reaction produced is then visible in an empty chamber downstream of the reaction layer and the materials are retained in this chamber by a liquid lock disposed at the lower end of the testing tube.

The advantages achieved with this solution are particularly clear in that, with specifically suitable reagents, used with small air sample volumes, the smallest contaminant concentrations of gas, vapor or aerosol mixtures can be quantitatively measured in the air sample. The color intensity of the liquid, which has collected in a so-far empty tube chamber, can be evaluated directly through a comparison without the dilution effect of a carrier substance.

An advantageous, specific development of the invention for a quantitative determination of sulphuric acid aerosols is one having a breakable ampoule which is filled with a water-propanol-2-solution and further including a granular reagent layer having a grain size of 0.5 mm to 0.8 mm which is impregnated with a barium-chlorine-anilate of a concentration of 0.5%. This shows very clearly, that the already comprehensive test vial program continues to provide renewed, simple solutions for still existing problems and tasks. A prototype is described by the invention, within the framework of a test vial for the quantitative determination of sulphuric acid aerosols.

Accordingly, an object of the present invention is to provide an improved glass testing tube and an improved method of measuring gas, vapor and aerosol components in air wherein a breakable ampoule is arranged within a testing tube to expel a solid liquid which flows through a filter which has previously entrained the particles of the air to be tested and the dissolved solvent is passed into an indicating layer which communicates with an empty chamber which exposes for view a reactant color change and, wherein, the reagents are retained in this chamber by a liquid lock.

A further object of the present invention is to provide a testing device and a method of measuring gas, vapor and aerosol components in air which is simple in concept and economical to carry out.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the Drawing:
The only FIGURE of the drawing is a sectional view of a testing tube, constructed in accordance with the present invention.

DESCRIPTION OF THE PREFERRED EMBODIMENT

Referring to the drawing in particular, the invention embodied therein, comprises, a testing tube 12 made of glass, which includes breakable tips 13 and 14 at each end and which has a hose sleeve 15 around a portion thereof in which a breakable ampoule 1 is located. Ampoule 1 is held in position by a fastener 6 and a fastener 7 which permit air flow therethrough and to a filter 2 which entrains particles of materials in the gas which are to be tested.

After the tips are broken off and other gases are drawn in the direction of the arrow 11, through the testing tube 12, the solvent from ampoule 1 is liberated by breaking the ampoule to permit the solvent to flow through the filter and dissolve the entrained particles so that they are directed with the solvent into the reaction layer 3 of an inert quartz material having a color reactant substance such as barium-chlorine-anilate.

In accordance with a feature of the invention, downstream of the reactant layer 3, there is an empty tank chamber 4, which is defined between fastening elements 8 and 9 and a liquid lock formed of a hydrophobic paper 5 is located between the fastener 9 and a fastener 10, and it functions to retain the indicating substance in the chamber 4 for visible viewing of the color change.

A glass tube 12 with a breakable tip 13 and 14 at respective ends thereof has the normal outer dimensions of customary test vials. A filling and graduation, respectively, is in sequence with the flow-through direction 11; a breakable ampoule 1, a filter layer 2 and the granular reagent layer 3, followed by the empty tube chamber 4. Ampoule 1 is filled with a solution of water-propanol-2. The material of filter layer 2 is quartz glass cloth, and that of the granular reagent layer 3 is inert quartz with a grain size of 0.5 mm to 0.8 mm, impregnated with barium-chlorine-anilate of a 0.5% concentration.

The tube chamber 4, which is flooded by the air sample at the onset of the test, is closed off by means of a liquid lock 5 consisting of hydrophobic filter material. It closes with the entrance of the liquid into the previously empty tube chamber 4. The individual fillings of the test vial are held shake-proof by fastening elements 6 to 10. At the level of ampoule 1, glass tube 12 is covered with the slip-over hose sleeve 15.

The determination takes place in three operating steps:
 1. After breaking off the tips 13 and 14, the test vial is inserted into the gas detection pump, and about ten liters of test air is sucked up in the flow-through direction 11. Any sulphuric acid aerosols present in the air sample are thus retained in filter layer 2.
 2. Ampoule 1 is broken and the water-propanol-2 solution is directed into the direction of the filling layers, so that these are completely moistened. The sulphuric acid deposited in filter layer 2 is dissolved here and, together with the solution, it is passed on to reagent layer 3. A color reaction occurs there.
 3. After a reaction time of about one minute, the solution in ampoule 1 is renewed and, this time, it is directed from reaction layer 3 into the empty tube chamber 4. The intensity there of the clearly visible discoloration of the solution is proportional to the mass of dissolved sulphuric acid. The exact sulphuric acid concentration in the air sample is determined by a comparison with a color standard.

While a specific embodiment of the invention has been shown and described in detail to illustrate the application of the principles of the invention, it will be understood that the invention may be embodied otherwise without departing from such principles.

What is claimed is:

1. A method of measuring gas, vapor and aerosol components in an air or gas sample, using a gas detecting device which includes a glass tube having openable ends for the flow of gas therethrough, and through a filter therein which entrains components to be measured, and further including a reaction layer in the tube downstream of a breakable ampoule having a liquid solvent therein for dissolving the entrained substances, further including an empty chamber portion through which the solvent liquid is directed after passing through the reaction layer in the tube, and further including a liquid lock downstream of the empty chamber portion, comprising, opening the tube to pass the gas to be tested therethrough and to entrain in the filter, particles of components to be measured, breaking the ampoule in the tube to direct a solvent through the filter to dissolve the entrained particles and directing the entrained particles and solvent through the reaction layer to achieve a color indication, and retaining the material having the color indication in the empty tank chamber using the liquid lock to prevent the escape thereof.

2. A device for measuring gas, vapor and aerosol components in an air or gas sample, comprising, a glass detecting tube which is breakable at each end, an ampoule of liquid solvent disposed in said tube adjacent one of said ends, a filter disposed in said tube adjacent said ampoule in a position to entrain particles of gas which pass therethrough, a granular reagent layer located downstream of said filter from said ampoule, a granular reagent layer made of impregnated inert granular quartz, means for holding said ampoule, said filter and said reagent layer in a position within said tube one after the other in the flow direction, means defining an empty tank chamber portion downstream of said reagent layer portion communicating with said reagent layer portion and a liquid lock in said tube downstream of said empty tank chamber.

3. A device for measuring gas, vapor and aerosol components in an air or gas sample, as claimed in claim 2, wherein said liquid lock comprises a hydrophobic paper disposed in said tube.

4. A device for measuring gas, vapor and aerosol components in an air or gas sample, as claimed in claim 2, wherein said breakable ampoule is filled with a water-propanol-2-solution and said granular reagent layer has a grain size of 0.5 mm to 0.8 mm and is impregnated with a barium-chlorine-anilate of a concentration of 0.5% for the testing of the presence of sulfuric acid aerosols.

* * * * *